(12) United States Patent
Ishikawa et al.

(10) Patent No.: US 10,821,230 B2
(45) Date of Patent: Nov. 3, 2020

(54) AUTOMATIC ADMINISTRATION INSTRUMENT FOR MEDICAL USE

(71) Applicant: PHC Holdings Corporation, Tokyo (JP)

(72) Inventors: Tokumi Ishikawa, Tokushima (JP); Tokumi Baba, Tokushima (JP)

(73) Assignee: PHC HOLDINGS CORPORATION, Tokyo (JP)

(*) Notice: Subject to any disclaimer, the term of this patent is extended or adjusted under 35 U.S.C. 154(b) by 77 days.

(21) Appl. No.: 16/108,481

(22) Filed: Aug. 22, 2018

(65) Prior Publication Data

US 2018/0353688 A1  Dec. 13, 2018

Related U.S. Application Data

(60) Continuation of application No. 15/644,105, filed on Jul. 7, 2017, now Pat. No. 10,363,368, which is a (Continued)

(30) Foreign Application Priority Data

Jul. 2, 2002 (JP) ................................. 2002-193057

(51) Int. Cl.
*A61M 5/20* (2006.01)
*A61M 5/24* (2006.01)
(Continued)

(52) U.S. Cl.
CPC ............ *A61M 5/20* (2013.01); *A61M 5/2066* (2013.01); *A61M 5/2448* (2013.01); *A61M 5/326* (2013.01);
(Continued)

(58) Field of Classification Search
CPC .. A61M 5/3157; A61M 5/20; A61M 5/31568; A61M 5/1723; A61M 5/172;
(Continued)

(56) References Cited

U.S. PATENT DOCUMENTS 4,613,328 A  9/1986 Boyd
4,741,732 A  5/1988 Crankshaw et al.
(Continued)

FOREIGN PATENT DOCUMENTS

EP  0 956 873  11/1999
GB  2 319 184  5/1998
(Continued)

OTHER PUBLICATIONS

International Search Report dated Oct. 7, 2003 in International Application No. PCT/JP03/08391.
(Continued)

*Primary Examiner* — Nilay J Shah
(74) *Attorney, Agent, or Firm* — Wenderoth, Lind & Ponack, L.L.P.

(57) ABSTRACT

An automatic administration instrument includes a syringe and a partition wall in the syringe which partitions the syringe into different rooms for respectively holding plural kinds of drug solutions or a drug and a drug solution. A partition-wall driver displaces the partition wall and an injection needle is connected to the syringe. A body cap attached to the administration instrument body so as to cover the injection needle. The syringe, the partition wall, and the body cap are configured such that displacing the partition wall dissolves or mixes the drug solutions or the drug and the drug solution in a state that the injection needle is covered by the body cap.

1 Claim, 5 Drawing Sheets

Related U.S. Application Data continuation of application No. 14/168,509, filed on Jan. 30, 2014, now Pat. No. 9,731,074, which is a continuation of application No. 13/587,271, filed on Aug. 16, 2012, now Pat. No. 8,679,055, which is a division of application No. 10/516,395, filed as application No. PCT/JP03/08391 on Jul. 2, 2003, now Pat. No. 8,298,171.

(51) Int. Cl.
    *A61M 5/32* (2006.01)
    *A61M 5/42* (2006.01)
    *A61M 5/315* (2006.01)
    *A61M 5/50* (2006.01)

(52) U.S. Cl.
    CPC ....... *A61M 5/422* (2013.01); *A61M 2005/206* (2013.01); *A61M 2005/208* (2013.01); *A61M 2005/2013* (2013.01); *A61M 2005/3152* (2013.01); *A61M 2005/5006* (2013.01); *A61M 2205/50* (2013.01); *A61M 2205/581* (2013.01)

(58) Field of Classification Search
    CPC .............. A61M 5/2033; A61M 5/3146; A61M 5/3158; A61M 5/3287; A61M 5/326; A61M 5/31571; A61M 2005/1726; A61M 2005/206; A61M 2005/208; A61M 2005/2013; A61M 2039/0244; A61M 2005/3143
    See application file for complete search history.

(56) References Cited

U.S. PATENT DOCUMENTS

| | | | |
|---|---|---|---|
| 4,950,246 | A | 8/1990 | Muller |
| 4,959,050 | A | 9/1990 | Bobo, Jr. |
| 5,176,502 | A | 1/1993 | Sanderson et al. |
| 5,176,643 | A | 1/1993 | Kramer et al. |
| 5,320,609 | A | 6/1994 | Haber et al. |
| 5,578,014 | A * | 11/1996 | Erez .......................... A61F 7/10 604/192 |
| 5,681,291 | A | 10/1997 | Galli |
| 5,688,252 | A | 11/1997 | Matsuda et al. |
| 5,891,086 | A | 4/1999 | Weston |
| 5,989,221 | A | 11/1999 | Hjertman |
| 6,099,503 | A | 8/2000 | Stradella |
| 6,159,161 | A | 12/2000 | Hodosh |
| 6,171,276 | B1 * | 1/2001 | Lippe ...................... A61M 5/20 128/DIG. 1 |
| 6,280,421 | B1 | 8/2001 | Kirchhofer et al. |
| 6,290,683 | B1 | 9/2001 | Erez et al. |
| 6,406,460 | B1 | 6/2002 | Hogan |
| 6,620,137 | B2 | 9/2003 | Kirchhofer et al. |
| 2001/0005781 | A1 * | 6/2001 | Bergens .............. A61M 5/2033 604/208 |
| 2001/0049496 | A1 | 12/2001 | Kirchhofer et al. |
| 2002/0016573 | A1 * | 2/2002 | Munk ..................... A61M 5/20 604/229 |
| 2002/0042592 | A1 | 4/2002 | Wilmot et al. |
| 2002/0058912 | A1 | 5/2002 | Hjertman |

FOREIGN PATENT DOCUMENTS

| | | |
|---|---|---|
| JP | 4-312469 | 11/1992 |
| JP | 6-7445 | 1/1994 |
| JP | 7-213610 | 8/1995 |
| JP | 8-150208 | 6/1996 |
| JP | 8-505543 | 6/1996 |
| JP | 11-503637 | 3/1999 |
| JP | 11-267206 | 10/1999 |
| JP | 2000-512523 | 9/2000 |
| JP | 2001-245974 | 9/2001 |
| JP | 2001/513371 | 9/2001 |
| JP | 2002-119593 | 4/2002 |
| WO | 93/02720 | 2/1993 |
| WO | 94/11041 | 5/1994 |
| WO | 94/27660 | 12/1994 |
| WO | 96/32974 | 10/1996 |
| WO | 97/48430 | 12/1997 |
| WO | 99/07425 | 2/1999 |
| WO | 99/56805 | 11/1999 |
| WO | 00/62839 | 10/2000 |
| WO | 01/17593 | 3/2001 |
| WO | 02/47746 | 6/2002 |

OTHER PUBLICATIONS

Supplementary Partial European Search Report dated Nov. 7, 2005 in corresponding European Application No. 03738633.1.
Supplementary European Report dated Dec. 23, 2005 in corresponding European Application No. 03738633.1.
Notice of Opposition dated Sep. 1, 2011 in corresponding European Patent Application No. EP 03738633.1.
European Office Action dated Mar. 26, 2014 in corresponding European Application No. 10 177 517.9-1662.
U.S. Office Action dated Feb. 7, 2020 in corresponding U.S. Appl. No. 16/108,468.
U.S. Office Action dated Jan. 31, 2020 in corresponding U.S. Appl. No. 16/108,483.
U.S. Office Action dated Feb. 28, 2020 in corresponding U.S. Appl. No. 16/108,493.
U.S. Office Action dated Mar. 306, 2020 in corresponding U.S. Appl. No. 16/108,532.
U.S. Office Action dated Feb. 7, 2020 in corresponding U.S. Appl. No. 16/108,436.
Extended European Search Report dated Jan. 9, 2020 in corresponding European Patent Application No. 19201377.9.
Final Office Action dated Jun. 18, 2020 in corresponding U.S. Appl. No. 16/108,483.
Final Office Action dated Aug. 24, 2020 in corresponding U.S. Appl. No. 16/108,493.
Final Office Action dated Aug. 24, 2020 in corresponding U.S. Appl. No. 16/108,532.

* cited by examiner

AUTOMATIC ADMINISTRATION INSTRUMENT FOR MEDICAL USE

This application is a continuation of application Ser. No. 15/644,105, filed Jul. 7, 2017, now Pat. No. 10/363,368, which is a continuation of application Ser. No. 14/168,509, filed Jan. 30, 2014, now Pat. No. 9,731,074, which is a continuation of application Ser. No. 13/587,271, filed Aug. 16, 2012, now U.S. Pat. No. 8,679,055, which is a divisional application of Ser. No. 10/516,395, filed Dec. 2, 2004, now U.S. Pat. No. 8,298,171, which is a 371 application of PCT/JP2003/008391, filed Jul. 2, 2003.

TECHNICAL FIELD

The present invention relates to an automatic administration instrument for medical use, which is used for administering drug solutions.

BACKGROUND ART

Conventionally, an administration instrument for medical use is often used when a drug solution such as growth hormone, insulin, or the like is administered. Generally, when using the administration instrument, a doctor or a nurse performs administration in a hospital or the like, and a patient or his family performs administration at home. The administration is carried out by inserting a needle into some region on the skin, and the angle of the needle insertion into the skin and the speed of the needle insertion as well as the speed at which the drug solution is injected after the needle insertion depend on the skill level of a person who performs the administration.

FIG. 5 is a block diagram illustrating the inside of an electric injector which is currently used in dentistry. The principle of administration of drug solutions will be described with reference to FIG. 5. Now, a syringe 103 filled with a drug solution is set in a cartridge holder 102 attached to a main body 110.

When pressing a SW1, a motor 111 normally rotates, and the torque is reduced by a reduction gear box 109 which is directly connected to the motor 111 to rotate a reduction gear main-shaft 108 of the reduction gear box 109. An end of the reduction gear main-shaft 108 engages with a gear 106 through a rotary disc 107 to rotate the gear 106. Further, the gear 106 engages with a gear 105 and thereby the torque of the gear 106 propagates to the gear 105. A gear 105a is provided coaxially with the gear 105 so as to engage with a rack 104a which is provided in the lower right half of a push piston 104 from the center thereof. When the gear 105 rotates, the gear 105a also rotates in the same direction as the gear 105, and consequently, the push piston 104 is moved in the direction of the injection needle 113, whereby the drug solution in the syringe 103 is pushed out of the injection needle 113.

During injecting, air is removed in the above-described operation, and thereafter, the injection needle 113 is inserted into a target region, and the drug solution is administered. In FIG. 5, SW2 denotes a switch for reverse rotation of the motor 111, and 112 denotes a battery for driving the motor 111.

Up to this point the conventional electric injector for automatically administering a drug solution has been described.

Next, a typical administration instrument for medical use in which a drug and a drug solution are dissolved and mixed, which has conventionally been employed, will be described with reference to FIG. 6. In the administration instrument for medical use shown in FIG. 6, when it is used, a drug and a drug solution are mixed and dissolved by manual operation and then injected. In FIG. 6, constituents that are substantially identical to those shown in FIG. 5 are given the same reference numerals.

Now, a syringe 103 is set in a cartridge holder 117, and the syringe 103 contains a powder preparation 114 and a drug solution 127 which are placed in different rooms separated by a rubber 116 and a rubber 118. An injection needle 113 attached to an end of the syringe 103 is provided with a needle cap 101. In this state, the injection needle 113 is directed upward and an injection button 120 is pushed toward the injection needle 113. Then, the push piston 119 pushes the rubber 118, the rubber then pushes the drug solution 127, and the rubber 116 moves toward the injection needle 113 with the pressure at which the drug solution 127 is pushed. When the rubber 116 reaches a position slightly ahead of a protrusion 115 of the syringe, the drug solution 127 goes over the rubber 116, passes the syringe protrusion 115, and starts to flow into the room of the powder preparation 114. The injection button 120 is further pushed, and then the drug solution 127 continuously flows into the room of the powder preparation 114. After all the drug solution 127 flows into the room of the powder preparation 114, the rubber 118 contacts the rubber 116.

Next, for fully mixing and dissolving them, the injection needle 113 is directed upward in the above-mentioned state and is slightly shaken. Next, with the injection noodle 113 being directed upward, the needle cap 101 is removed and the injection button 120 is pressed, thereby releasing air. After the air releasing, the injection needle 113 is inserted into a region of the body at which the drug solution is to be administered, and the injection button 120 is pressed, whereby the drug solution is administered into the region. As described above, in the administration instrument shown in FIG. 16, the processes from the mixing and dissolving of the drug and drug solution to the administration thereof are manually performed.

However, in the conventional administration instrument for medical use, no matter how much a person is skilled in achieving the angle to the skin and the speed during needle insertion as well as the speed of injecting the drug solution and the speed of removing the needle after the needle insertion, the person who does the administration is merely a human being, and therefore, the above-mentioned angle and speeds cannot be prevented from being varied depending on the physical condition and the like at that time. Since a person who administers the drug solution and a person who is given the drug solution are both human beings, the body sizes are different and the physical conditions at the administration are not always the same. Therefore, it is difficult to administer the drug solution in the same manner every time. Therefore, it is not always possible to perform administration with reduced pain.

Particularly, since the electric injector shown in FIG. 5 is a grip type injector, the user must grip and support its body by one hand as well as keep on pressing the SW1 throughout administration. Further, since the injector is large in shape and a battery 112 is heavy in weight, a great physical strain is imposed on the person who performs administration and, therefore, it is difficult to perform self-administration using this injector.

Further, in the mixing and dissolving type administration instrument shown in FIG. 6, since the dissolving operation is manually performed, it is necessary to watch the dissolving condition with great care as well as perform the dissolving with discretion. Further, proper mixing cannot be performed unless the injection needle is shaken in a vertical orientation even after the dissolving. This is a very troublesome work for a patient having bad eyesight.

Further, a patient may have a fear about seeing the injection needle until just before administration, and this may cause a mental strain to the patient.

As described above, the needle insertion itself imposes physical and mental strains on the patient and, in some cases, seriously affects the body of the patient, which might lead to life-threatening danger.

The present invention is made to solve the above-described problems and has an object of providing an administration instrument for medical use which automatically performs needle insertion, administration, and needle removal, and further, automatically performs dissolving, mixing, and air-releasing when it is a dissolving and mixing type administration instrument, and still further, has a construction in which an injection needle is kept unseen from the outside until just before needle insertion, thereby reducing physical and mental strains on patients and realizing administration under more stable conditions.

DISCLOSURE OF THE INVENTION

An automatic administration instrument for medical use according to the present invention is provided with means for automatically inserting an injection needle into a skin, and means for automatically removing the injection needle from the skin, and injection is carried out under the state where a part of the body of the administration instrument is pressed against a body region of a patient to be subjected to administration. Therefore, an angle, a depth, and a speed at which needle insertion or needle removal is carried out can be controlled, thereby reducing a possibility that administration is influenced by variations in the level of skill, daily physical condition, or body size among individuals.

Further, in the automatic administration instrument for medical use according to the present invention, the speed at which the injection needle is automatically inserted into the skin or the speed at which the injection needle is automatically removed from the skin is made variable, and the amount of drug solution to be injected per unit time during administration can be arbitrarily set, and further, the injection needle is not visible from the outside until needle insertion is completed. Therefore, the pain of the patient to which the drug solution is administered is reduced during needle insertion, administration, and needle removal, and the fear of the patient is also reduced, whereby administration can be carried out in a stable manner, resulting in reductions in physical and mental burdens.

Further, when the automatic administration instrument for medical use according to the present invention is an administration instrument that employs plural drug solutions to be mixed, or a drug and a drug solution to be dissolved and mixed, the mixing or dissolving is automatically carried out, and further, a syringe is automatically shaken in the administration instrument body after the mixing or dissolving is completed. Therefore, the patient is relieved of the inconvenience of the mixing or dissolving operation, and further, the drug solutions can be mixed with higher reliability, whereby the drug solution itself can be used in the optimum state. Further, since air-releasing or the like is also automatically carried out, it becomes unnecessary to check air-releasing, thereby reducing the inconvenience of the air-releasing operation.

Furthermore, in the automatic administration instrument for medical use according to the present invention, when the patient forgets about attaching the injection needle when performing dissolving or administration, the operation of pushing out the drug solution is stopped, thereby preventing the risk of cracking of the syringe, inverse leakage of the drug solution, or the like.

DETAILED DESCRIPTION OF THE INVENTION

Hereinafter, an embodiment of the present invention will be described with reference to FIGS. 1 to 4.

Figure 1:
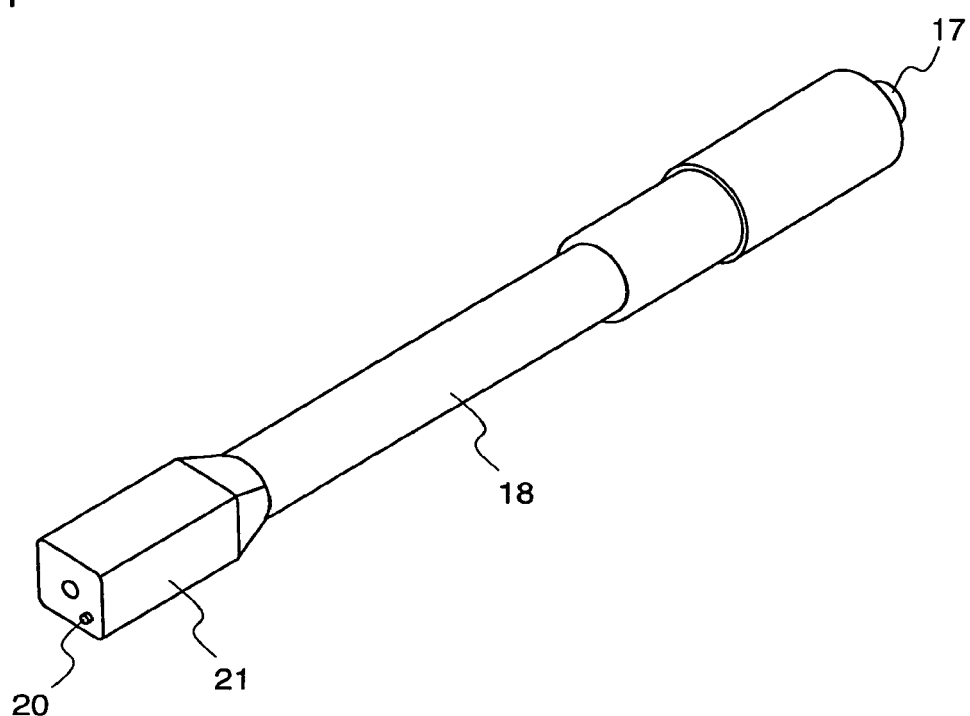
FIG. 1 is a perspective view of an automatic administration instrument for medical use according to a first embodiment of the present invention.
Figure 2:
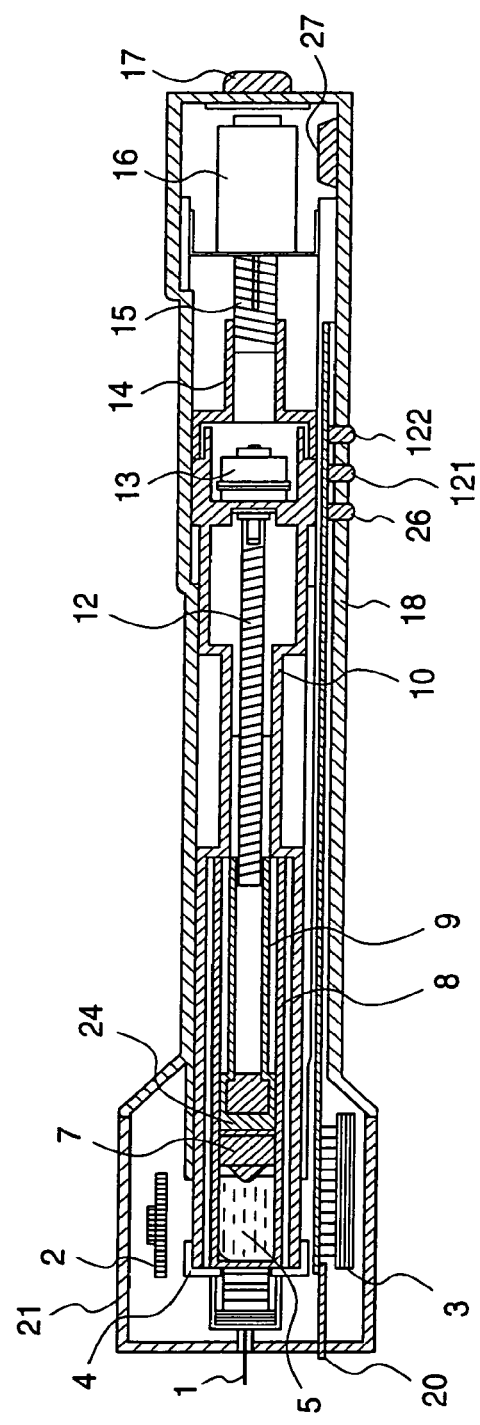
FIG. 2 is a cross-sectional view of the automatic administration instrument for medical use.
Figure 3:
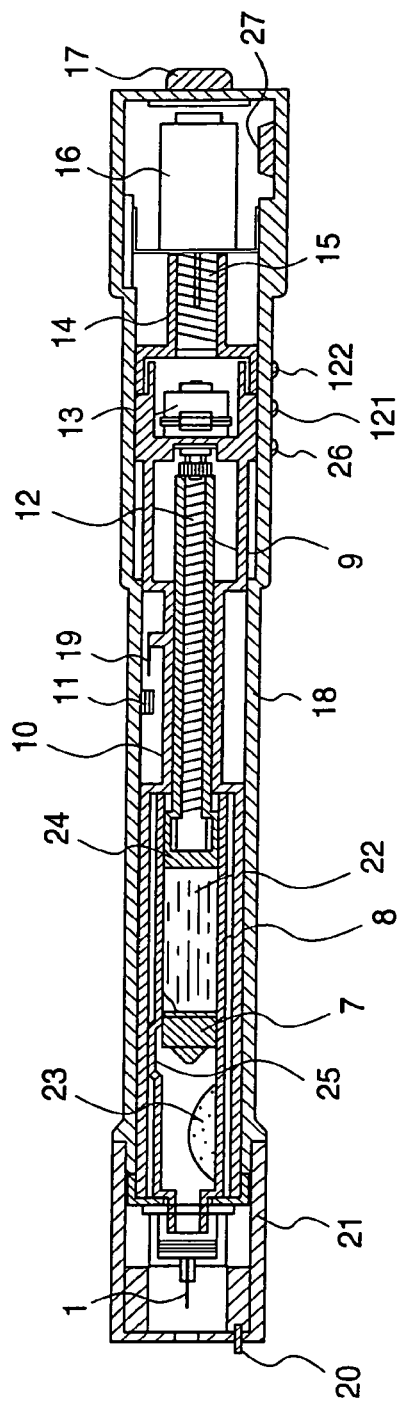
FIG. 3 is a cross-sectional view of an automatic administration instrument for medical use according to another embodiment of the present invention.
Figure 4:
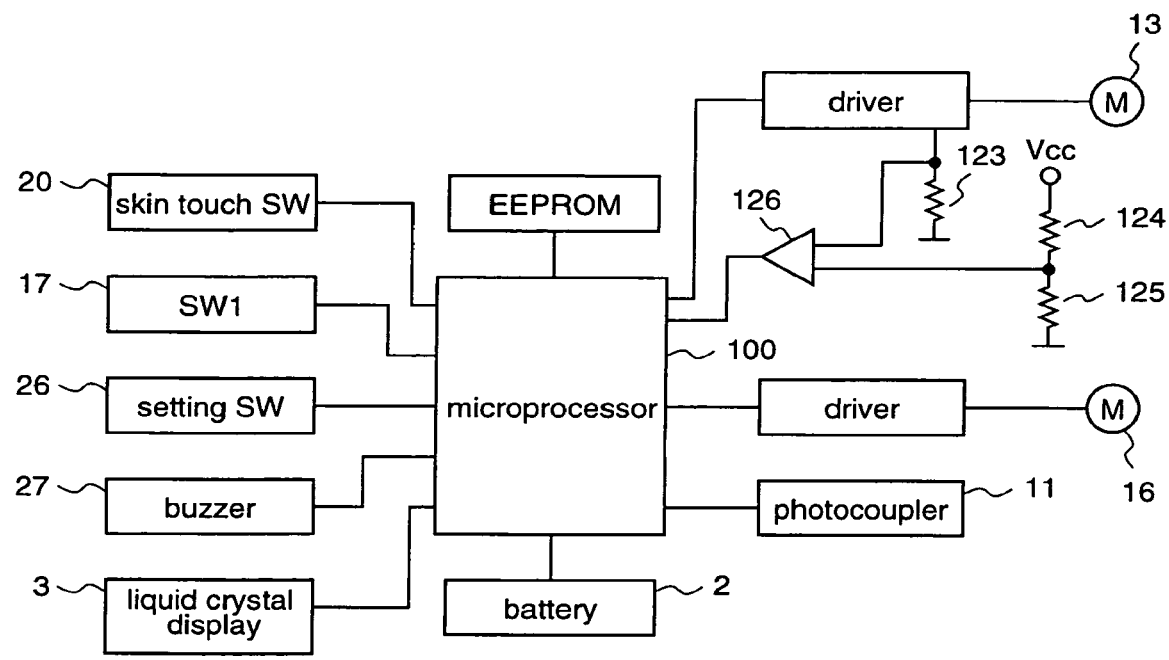
FIG. 4 is a block diagram illustrating the automatic administration instrument for medical use according the embodiment of the present invention.
Figure 5:
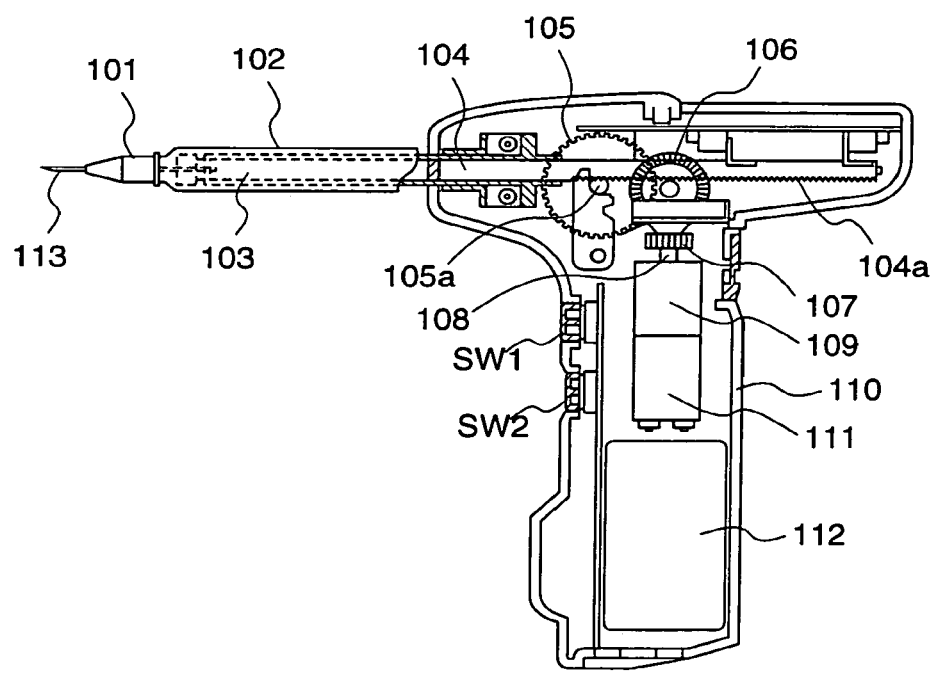
FIG. 5 is a block diagram illustrating an internal construction of the conventional electric injector.

FIG. 1 is a perspective view illustrating an external view of an automatic administration instrument for medical use according to an embodiment of the present invention, FIG. 2 is a cross-sectional view for explaining the internal structure of the automatic administration instrument for medical use, FIG. 3 is a cross-sectional view for explaining the internal structure of an automatic administration instrument for medical use according to another embodiment of the present invention, and FIG. 4 is a block diagram for explaining the embodiment of the present invention.

First of all, the construction and operation of an automatic administration instrument for medical use which is capable of automatic needle insertion and automatic needle removal will be described with reference to FIG. 1, FIG. 2, and FIG. 4.

In FIG. 1, reference numeral 18 denotes a body of the automatic administration instrument for medical use, numeral 17 denotes a switch for making the administration instrument perform insertion and removal of an injection needle, numeral 21 denotes a body cap that covers the injection needle, and numeral 20 denotes a skin touch switch for detecting that the administration instrument body 18 is pressed against a body region where administration is to be carried out.

In FIG. 2, an inner case 10 to which a syringe 8 filled with a drug solution 5 is attached is set in the body 18. An injection needle 1 is set at an end of the inner case 10. Further, the injection needle 1 is housed in a body cap 21 and is invisible from the outside. In FIG. 2, however, the injection needle is visible because FIG. 2 shows the position of the needle during needle insertion. Further, a battery 2 and a liquid crystal display 3 are also housed in the body cap 21.

Now, the user holds the body 18 by hand, presses the skin touch switch 20 against a target region on his/her body, and presses the switch 17. Then, an axis of a motor 16 starts to rotate, and thereby a movable screw that is directly connected to the axis of the motor 16 rotates. A screw thread is formed on the surface of the movable screw 15 so as to engage with a thread formed inside the inner cap 14. The inner cap 14 is engaged with a part of the inner case 10 by screws, and is freely movable by a predetermined stroke in the longitudinal direction of the body 18, in the body 18 united with the inner case 10.

That is, in this construction, as the axis of the motor 16 rotates, the movable screw 15 rotates. The rotation is converted into a thrust that moves the inner case 10 toward the tip of the injection needle 1 in the body 18 by the inner cap 14, and consequently, the injection needle 1 is protruded from the body cap 21 toward the skin and inserted into the skin.

When administration of the drug solution is ended, the motor 16 rotates backward, and the injection needle 1 is housed into the body 18. That is, the needle 1 is removed from the skin.

It has been known that the higher the speed of inserting and removing the injection needle is, the lesser the patient feels pain. While in this embodiment these operations are carried out at an instant of 0.05 sec or below during actual administration, the operation speed is variable and settable by a setting switch 26. Further, a series of operations and settings described above are carried out by sending signals to a microprocessor 100 shown in FIG. 4 to be judged and instructed by the microprocessor 100.

Since, for safety, the circuit is constructed so that the actual needle insertion is not carried out unless the skin touch switch 20 is pressed, the needle insertion cannot be carried out unless the skin touch switch 20 is pressed against the target skin region. Further, the needle removal is carried out by rotating the motor 16 backward after the microprocessor 100 judges that the administration is completed. Also the needle removal is carried out at an instant of 0.05 sec or below, like the needle insertion.

In the above-mentioned construction, the operation of injecting the drug solution is carried out as follows.

With reference to FIG. 2, the user holds the body 18 by hand, presses the skin touch switch 20 against a target region where administration is to be carried out, and pushes the switch 17. Then, the injection needle 1 is inserted into the skin. When about 0.5 sec has passed after the needle insertion, the motor 13 starts to rotate, and the rotation propagates to the shaft screw 12. The inside of a drug solution push piston 9 is engaged with a screw thread formed at the surface of a shaft screw 12, whereby the piston 9 is movable forward and backward in the syringe 8 when the shaft screw 12 rotates. Therefore, when the shaft screw 12 rotates, the drug solution push piston 9 is pushed forward. When the drug solution push piston 9 moves forward, it presses the rubber 24 and the rubber 7, and further, the drug solution 5 is pushed out of the tip of the injection needle 1 to be administered into the skin.

However, when the skin touch switch 20 is not pressed, that is, when the body 18 is not pressed against the skin, no needle insertion nor injection of drug solution are carried out even if the switch 17 is pressed, as already described above. Once the switch 17 is pressed, it continues to operate.

The time until the motor 13 starts to operate after needle insertion, and the duration of drug injection by the motor 13, i.e., the amount of drug solution to be injected, are previously incorporated in the microprocessor 100 shown in FIG. 4, and these operations are carried out according to instructions from the microprocessor 100.

Further, replacement of the syringe 8 is carried out as follows.

Figure 6:
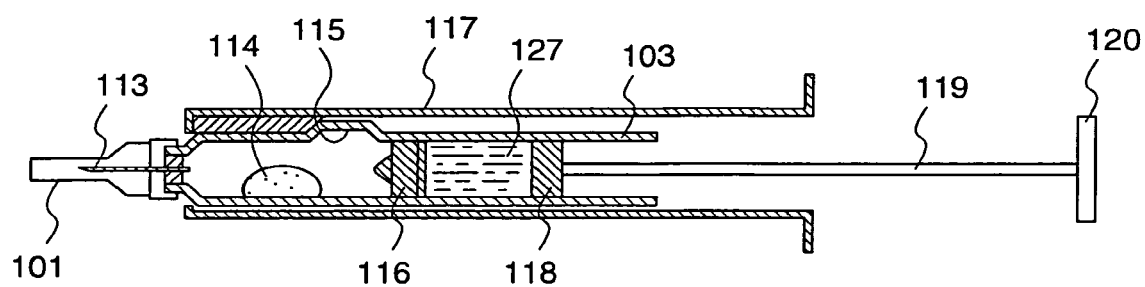
FIG. 6 is a cross-sectional view of a dissolving and mixing type automatic administration instrument for medical use according to conventional example.

After administration, the injection needle 1 is surely housed in the body 18. When the reset switch 122 is pressed in this state, the motor 13 and the shaft screw 12 rotate so as to pull the drug solution push piston 9 back into the body. Then, the body cap 21 is removed in the state where the drug solution push piston 9 is housed in the body, the needle cap 101 (similar to that shown in FIG. 6) is attached to the injection needle 1, and the injection needle 1 is twisted to be removed. Next, the syringe cap 4 is removed, and the syringe 8 is removed so as to be replaced with a new one. After syringe replacement, the syringe cap 4 is set, and the injection needle 1 covered with the needle cap 101 is set. Thereafter, the needle cap 101 is removed, and the body cap 21 is attached to the body 18, whereby the administration instrument goes into the stand-by for administration.

Next, a description will be given of automatic dissolving, automatic mixing (shaking), automatic air-releasing, and automatic administration, with reference to FIGS. 3 and 4.

The inside of the syringe 8 is partitioned by the rubber 7 and the rubber 24 into two rooms, and the respective rooms are filled with the drug solution 22 and the powder preparation 23. Further, the injection needle 1 is previously attached to the tip of the syringe 8.

When the user holds the body 18 by hand and presses the dissolving switch 121 with the injection needle 1 turning upward, the motor 13 rotates, and the shaft screw 12 directly connected to the axis of the motor 13 rotates. A screw thread is formed on the surface of the shaft screw 12 so as to engage with a thread formed inside the drug solution push piston 9, and the tip of the drug solution push piston 9 is fixed to the rubber 24 with a screw.

Accordingly, when the shaft screw 12 rotates, the rubber 24 united with the drug solution push piston 9 starts to move toward the tip of the injection needle. That is, when the axis of the motor 13 rotates, the shaft screw 12 rotates, and the rotation is converted into a thrust that moves the rubber 24 in the syringe 8 toward the injection needle 1 by the drug solution push piston 9.

Next, when the rubber 24 is pushed, the drug solution 22 is compressed and pushes the rubber 7 forward. When the rubber 7 reaches a position slightly ahead of a protrusion 25 of the syringe, the drug solution 22 passes through the space that is formed by the protrusion 25 of the syringe and, further, goes over the rubber 7 and flows into the room where the powder preparation 23 exists. At this time, the rubber 7 does not move even when the rubber 24 is pressed toward the injection needle 1 until all of the drug solution 22 flows into the room of the powder preparation 23.

After the rubber 24 is pressed toward the injection needle 1 and all of the drug solution 22 flows into the room of the powder preparation 23, the rubber 24 contacts the rubber 7. On the other hand, the drug solution 22 that has flowed into the room of the powder preparation 23 starts to gradually dissolve the powder preparation 23. The microprocessor 100 shown in FIG. 4 monitors the time from when the motor 13 starts to rotate to when all of the drug solution 22 flows into the room of the powder preparation 23. Up to this point the automatic dissolving has been described.

As described above, since the microprocessor 100 shown in FIG. 4 monitors the time required for a series of operations up to the automatic dissolving, it instructs automatic mixing (shaking) after the automatic dissolving is completed.

Hereinafter, this operation will be described.

The body 18 is positioned so that the injection needle 1 turns upward. In FIG. 4, when the microprocessor 100 judges that the automatic dissolving is completed, the microprocessor 100 outputs an instruction to rotate the motor 16. When the motor 16 rotates, the movable screw 15 directly connected to the axis of the motor 16 rotates.

A screw thread is formed on the surface of the movable screw 15 so as to engage with a thread formed inside the inner cap 14. The inner cap 14 is fixed to a part of the inner case 10 with a screw, and is freely movable in combination with the inner case 10, by a predetermined stroke in the direction parallel to the longitudinal direction of the body 18, in the body 18. That is, when the axis of the motor 16 rotates, the movable screw 15 rotates, and the rotation is converted into a thrust that moves the inner case 10 forward in the body 18 by the inner cap 14.

A plate-shaped protrusion 19 is formed on a part of the inner case 10. Further, a photocoupler 11 is formed on the inside of the body 18. As the inner case 10 moves toward the injection needle 1 with rotation of the motor 16, the plate-shaped protrusion 19 also moves in the same direction. When the plate-shaped protrusion 19 reaches the position of the photocoupler 11, the microprocessor 100 outputs an instruction to rotate the motor 16 in the direction inverse to the previous rotation, according to a detection signal of the photocoupler 11. Then, the inner case 10 moves up to the initial position. When the inner case 10 reaches the initial position, the microprocessor 100 again outputs an instruction to normally rotate the motor 16 as before. Then, the inner case 10 starts to move toward the injection needle 1.

By repeating the above-mentioned operation several times, the inner case 10 is shaken. Consequently, the syringe 8 attached to the inner case 10 is shaken, whereby the dissolved drug solution in the syringe 8 is shaken.

The shaking time of the syringe 8 and the number of times the syringe 8 is shaken (for example, 10 sec or below, and five to twenty times) have previously been incorporated as a program in the microprocessor 100 so that an optimum state can be obtained according to the drug solution to be handled. The stroke during the shaking is made so that the injection needle 1 never goes out of the body cap 21 attached to the body 18.

Next, automatic air-releasing and automatic administration will be described.

Initially, automatic air-releasing is incorporated as a program in the microprocessor 100 so as to be carried out subsequently to the automatic shaking.

During the air-releasing, the body is positioned with the injection needle 1 turning upward, as in the dissolving and shaking. The air-releasing is carried out with the injection needle 1 protruding from the body cap 21.

After the shaking, the microprocessor 100 outputs an instruction to normally rotate the motor 16. Then, as described above, the movable screw 15 rotates, and the inner cap 14 moves the inner case 10 toward the injection needle 1, and consequently, pushes the injection needle 1 out of the body cap 21. During the air-releasing, even if the plate-shaped protrusion 19 formed at a part of the inner case 10 passes the photocoupler 11 formed on the inside of the body 18, the microprocessor 100 does not accept a signal at this time.

At a point in time when the injection needle 1 goes out of the body cap 21, the microprocessor 100 stops rotation of the motor 16, and then outputs an instruction to normally rotate the motor 13. As already described for the automatic dissolving, when the motor 13 normally rotates, the rotation makes the shaft screw 12 rotate, and makes the drug solution push piston 9 move toward the injection needle 1.

Since the operation up to the shaking has been ended, the rubber 7 and the rubber 24 contacting each other moves toward the injection needle 1, pushes out the drug solution in the syringe 8, and further, pushes out the air in the syringe 8. Since the amount of air to be pushed out at this time depends on the amount of operation of the drug solution push piston 9, i.e., the rpm of the motor 13, the rpm of the motor 13 is previously incorporated in the microprocessor 100 as a program.

Next, automatic administration will be described. The user holds the body 18 by hand, and presses the skin touch switch 20 against a target region, and presses the switch 17. Then, automatic needle insertion is carried out. Since the detail has already been described, repeated description is not necessary.

After the automatic needle insertion, the microprocessor 100 outputs an instruction to normally rotate the motor 13. Then, the shaft screw 12 rotates, and the drug solution push piston 9 pushes the rubber 24 and the rubber 7, and further, pushes the drug solution. The drug solution is administered to the skin through the inside of the injection needle 1. The speed of administering the drug solution at this time can be variably set by the setting switch 26. Further, since the motor 13 is controlled at a constant speed by the microprocessor 100, it is possible to make the amount of drug solution to be injected per unit time constant.

When the skin touch switch is removed from the skin during the administration, the microprocessor 100 outputs an instruction to stop the rotation of the motor 13, whereby the drug solution push piston 9 stops, and consequently, injection of the drug solution from the needle 1 stops. Further, the injection needle 1 goes into the automatic needle removal state after a few seconds from when rotation of the motor 13 stops, and then it is housed in the body 18. At this time, the reason why the injection needle 1 is left for a few seconds is because the drug solution may leak from the tip of the injection needle 1 due to pressure that has been applied to the drug solution push piston 9 even if the piston 9 is suddenly stopped during the administration. The time has previously been stored in the microprocessor.

After the administration is completed, the microprocessor 100 outputs an instruction to perform the operation of automatic needle removal. An appropriate time from the completion of administration to the automatic needle removal should be about 6 sec, considering existing data that the time from when injection of the drug solution is stopped to when leakage of the drug solution from the tip of the needle is completely stopped is about 5 sec.

A series of operations from the automatic needle insertion and the automatic administration to the automatic needle removal may be performed by only pressing the skin touch switch 20 against the skin without pushing the switch 17. For this purpose, the microprocessor 100 should monitor the time periods required for the respective operations from when the skin touch switch 20 touches the skin, whereby all of the operations can be carried out at appropriate timings. Further, the microprocessor 100 may sound a buzzer 27 with varying the tone according to the timings of the respective operations, i.e., needle insertion, administration, completion of administration, needle removal, etc., whereby a person having bad eyesight as well as a person having normal eyesight can recognize the operation state by the sound, and they can use the administration instrument with peace in mind.

Further, if the user forgets about attaching the injection needle 1 when performing dissolving or administration, dissolving or administration are prevented by the operation as follows.

This operation will be described with reference to FIGS. 2, 3, and 4.

With reference to FIG. 4, the driver of the motor 13 is provided with a detection resistor 123 for converting a current that flows in the motor 13 into a voltage. The voltage is compared with a reference voltage that is previously set by a reference voltage setting resistor 124 and a reference voltage setting resistor 125 in a comparator 126. When the user presses the switch 17 to perform dissolving or administration without the injection needle, the motor 13 tries to normally rotate in such a direction that the drug solution push piston 9 pushes out the drug solution 9. However, in the rooms filled with the drug solution 5 (22) and the powder preparation 23, respectively, there is no way to make the air or the drug solution escape because the injection needle 1 is not attached, and thereby the pressure increases suddenly. However, the motor 13 tries to continue the rotation, more current flows into the detection resistor 123, and thereby the voltage of the detection resistor 123 increases. When the voltage of the detection resistor 123 exceeds the voltage that is set by the reference voltage setting resistor 124 and the reference voltage setting resistor 125, the output of comparator 126 instructs the microprocessor 100 to stop the motor 13. Of course, a program for giving the above-mentioned instruction is previously incorporated in the microprocessor 100.

APPLICABILITY IN INDUSTRY

As described above, the automatic administration instrument for medical use according to the present invention is useful as an administration instrument for administering drug solutions such as growth hormone, insulin, and the like.

What is claimed is:

1. An automatic administration instrument for medical use for injecting a drug solution filled in a syringe, the automatic administration instrument comprising:

a body for housing the syringe and an injection needle;

a first motor for sliding the syringe within the body in a first direction and in a second direction opposite to the first direction, the first direction being a direction in which a tip of the injection needle faces when the injection needle protrudes from the body;

a second motor for operating the syringe to administer the drug solution;

a skin touch switch which detects whether the body contacts a body region of the patient to which the drug solution is to be administered; and an administration switch provided on the body, the administration switch being configured to activate the first motor and the second motor in sequential order when the administration switch is operated while the skin touch switch detects that a part of an exterior of the body is pressed against the body region the patient to which the drug solution is to be administered, wherein the administration switch activates the first motor to drive the syringe in the first direction such that the injection needle protrudes from the body to perform the injection needle insertion into the body region of the patient while the part of the exterior of the body is pressed against the body region of the patient, and thereafter activates the second motor to administer the drug solution, and after the drug solution is administered reactivates the first motor to slide the syringe in the second direction such that the protruding injection needle is retracted into the body while the part of the exterior of the body is pressed against the body region of the patient, wherein there is a period of time from the completion of administration by stopping the second motor to the start of an automatic needle removal operation by reactivating the first motor, and wherein, when the skin touch switch is removed from the skin during the administration of the drug solution, the second motor stops, and after the period of time from the stop of the second motor, the first motor reactivates the automatic needle removal operation.

\* \* \* \* \*